(12) United States Patent
Sattler et al.

(10) Patent No.: US 9,457,349 B2
(45) Date of Patent: Oct. 4, 2016

(54) PACKAGING CASSETTE FOR REAGENT CARRIERS

(75) Inventors: Stephan Sattler, Stamberg (DE); Reinhold Krämer, Peissenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/168,553

(22) Filed: Jul. 7, 2008

(65) Prior Publication Data

US 2009/0008395 A1 Jan. 8, 2009

Related U.S. Application Data

(63) Continuation of application No. PCT/EP2007/000268, filed on Jan. 12, 2007.

(30) Foreign Application Priority Data

Jan. 13, 2006 (DE) .................. 10 2006 001 881

(51) Int. Cl.
  *B65D 1/24* (2006.01)
  *B01L 3/00* (2006.01)
  *G01N 35/00* (2006.01)

(52) U.S. Cl.
  CPC ........ *B01L 3/50855* (2013.01); *B01L 3/50853* (2013.01); *B01L 2200/16* (2013.01); *B01L 2300/043* (2013.01); *B01L 2300/047* (2013.01); *G01N 2035/00089* (2013.01)

(58) Field of Classification Search
  USPC ............ 220/524, 507, 359.1, 526, 837, 375, 220/839; 206/558, 560
  See application file for complete search history.

(56) References Cited

U.S. PATENT DOCUMENTS

| | | | |
|---|---|---|---|
| 3,713,985 A | * | 1/1973 | Astle .................... B01L 3/5085 422/561 |
| 3,918,578 A | | 11/1975 | Cullen et al. |
| 4,741,441 A | | 5/1988 | Keffeler |
| 4,793,492 A | | 12/1988 | Halbich |
| 4,978,503 A | * | 12/1990 | Shanks et al. ................. 422/58 |
| 5,558,229 A | | 9/1996 | Halbich |
| 5,650,125 A | * | 7/1997 | Bosanquet .................... 422/548 |
| 5,735,406 A | * | 4/1998 | Keffeler ........................ 206/535 |
| 5,750,075 A | * | 5/1998 | Spike ............................ 422/558 |

(Continued)

FOREIGN PATENT DOCUMENTS

| DE | 19734135 A1 | 8/1997 |
|---|---|---|
| DE | 19734135 A1 | 2/1999 |

(Continued)

OTHER PUBLICATIONS

International Preliminary Report, Jan. 12, 2007, Appl. PCT/EP2007/000268, pp. 1-7.

(Continued)

*Primary Examiner* — Jeffrey Allen
(74) *Attorney, Agent, or Firm* — Dinsmore & Shohl LLP

(57) ABSTRACT

The invention concerns a packaging cassette for reagent carriers, which is characterized by a base housing containing connected adjacent compartments for reagent carriers, wherein the compartments are separated from one another by partitions and are opened individually, each compartment having its own sealing cover which enables the compartment to be re-sealed.

21 Claims, 2 Drawing Sheets

(56) References Cited

U.S. PATENT DOCUMENTS

| | | | |
|---|---|---|---|
| 5,863,800 A | 1/1999 | Eikmeier et al. | |
| 6,116,461 A | 9/2000 | Broadfield et al. | |
| 6,221,027 B1 * | 4/2001 | Pitesky | A61B 5/411 206/538 |
| 6,631,805 B2 * | 10/2003 | Bramen | 206/538 |
| 6,669,910 B1 * | 12/2003 | Bienhaus et al. | 422/102 |
| 6,682,704 B2 | 1/2004 | Bottwein et al. | |
| 6,730,494 B1 | 5/2004 | Toranto et al. | |
| 7,169,602 B2 | 1/2007 | Sandell | |
| 7,550,291 B2 | 6/2009 | Belz et al. | |
| 2002/0170911 A1 | 11/2002 | Lafond et al. | |
| 2003/0077207 A1 * | 4/2003 | Tyndorf et al. | 422/102 |
| 2004/0110275 A1 * | 6/2004 | Sandell | 435/287.1 |
| 2004/0151932 A1 * | 8/2004 | Galloway | 428/515 |
| 2004/0256963 A1 | 12/2004 | Affleck et al. | |
| 2005/0016873 A1 * | 1/2005 | Belfance et al. | 206/204 |
| 2005/0122010 A1 | 6/2005 | Kobayashi et al. | |
| 2006/0169603 A1 * | 8/2006 | Lancesseur et al. | 206/204 |

FOREIGN PATENT DOCUMENTS

| | | |
|---|---|---|
| DE | 10203940 A1 | 8/2003 |
| DE | 10309210 A1 | 9/2004 |
| DE | 10309211 A1 | 9/2004 |
| DE | 202005015260 U1 | 1/2006 |
| EP | 0642828 A1 | 8/1994 |
| EP | 0798228 A1 | 1/1997 |
| EP | 869083 A2 | 10/1998 |
| EP | 798228 A1 | 3/2001 |
| EP | 798228 B1 | 3/2001 |
| EP | 1285695 A2 | 2/2003 |
| FR | 2864826 | 7/2005 |
| WO | 9310454 A1 | 5/1993 |
| WO | 9907471 A1 | 2/1999 |
| WO | 03008103 A1 | 1/2003 |
| WO | 04001389 A1 | 12/2003 |
| WO | 2004074845 A2 | 9/2004 |

OTHER PUBLICATIONS

Search Report issued by the German Patent and Trademark Office with regard to the basic priority patent application DE 10 2006 001 881.8.

* cited by examiner

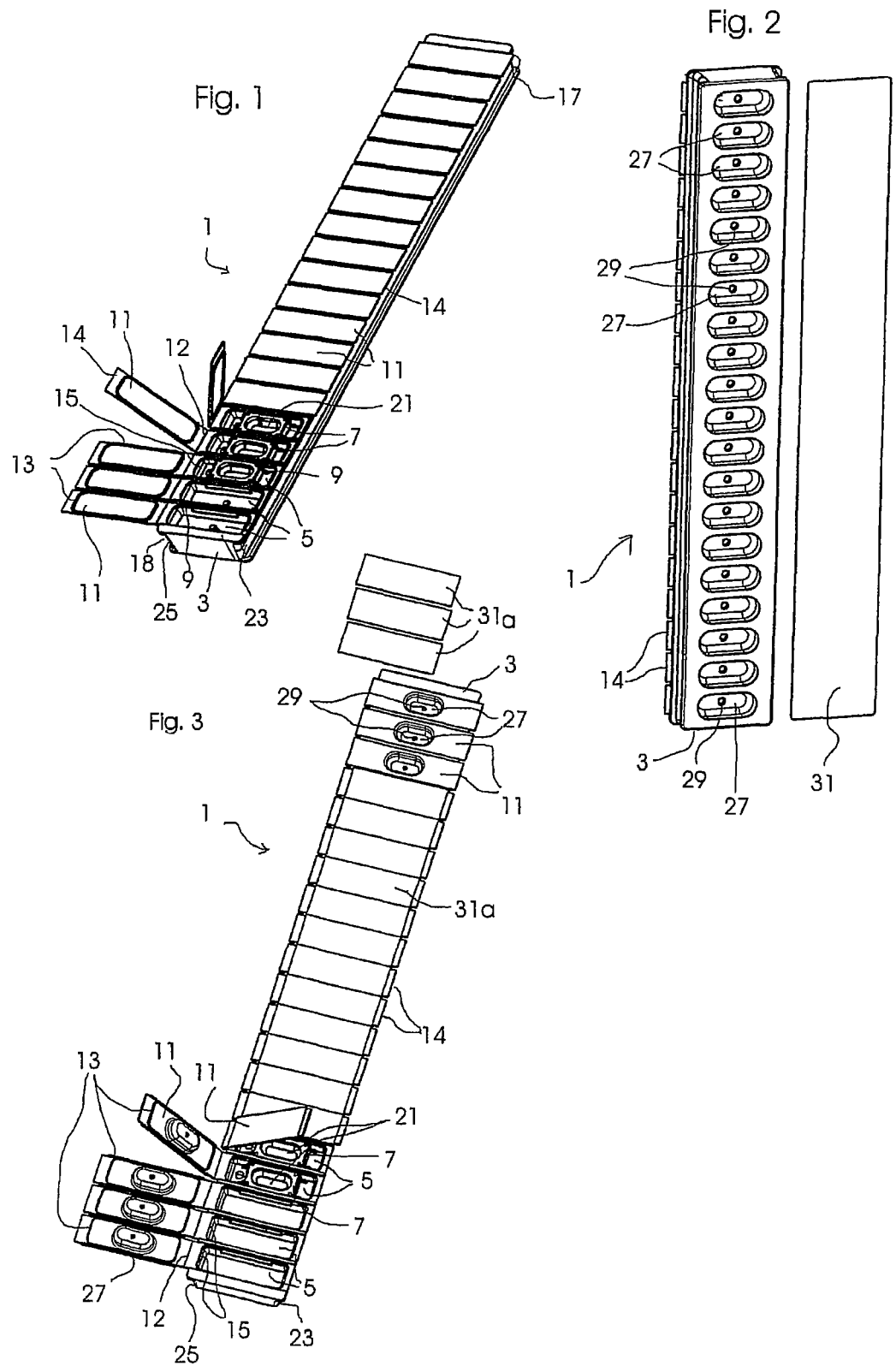

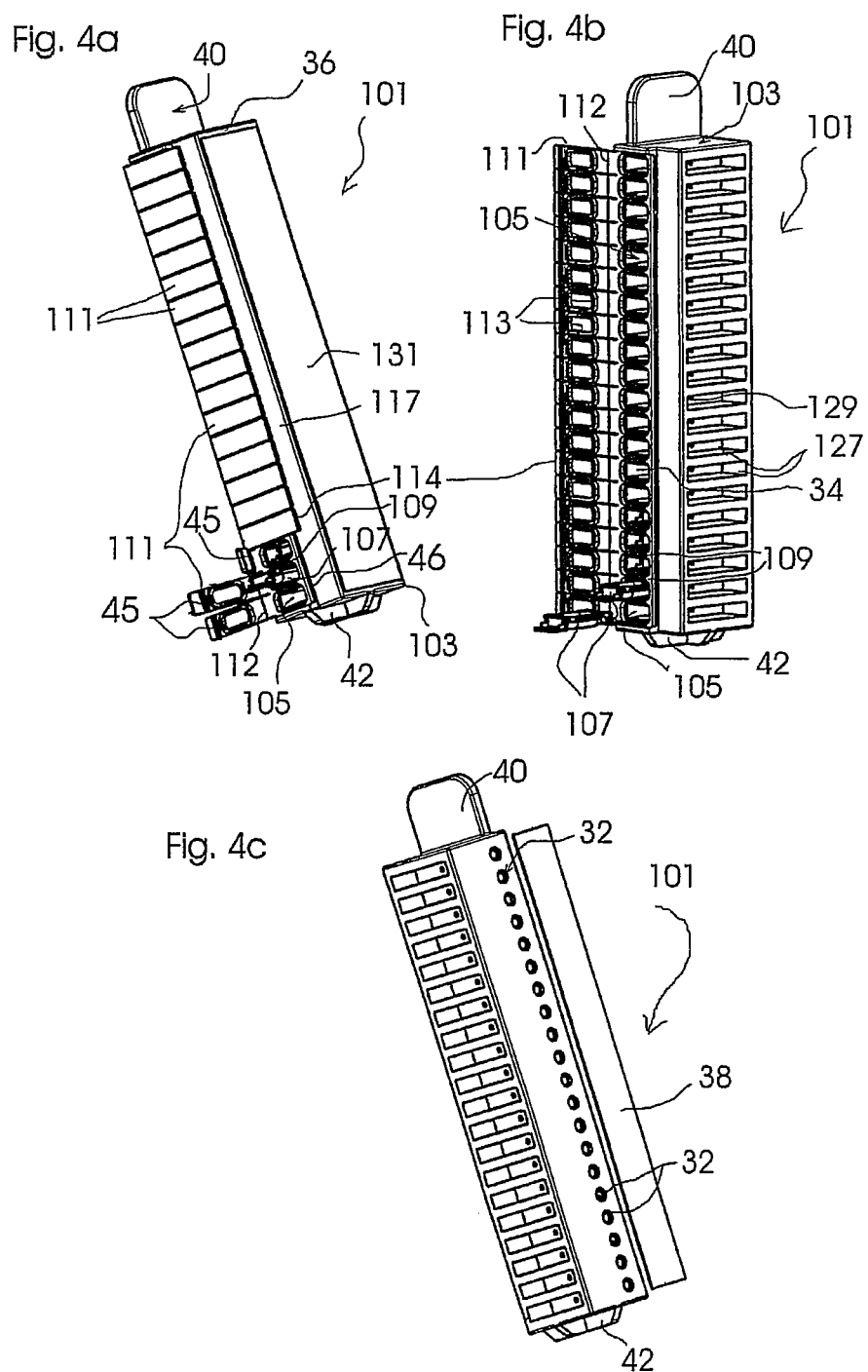

PACKAGING CASSETTE FOR REAGENT CARRIERS

CROSS REFERENCE TO RELATED APPLICATIONS

This application is a continuation of PCT application EP2007/000268, filed 12 Jan. 2007, which claims priority to German Application No. 10 2006 001 881.8, filed 13 Jan. 2006.

FIELD OF THE INVENTION

The invention concerns a packaging cassette for reagent carriers.

BACKGROUND OF THE INVENTION

Reagent carriers of the type that are under consideration here are for example test strips and preferably test chips e.g. biochips for detecting analytes in a sample liquid. They can for example be used for immunoassay applications in which binding reactions between reactants which are preferably immobilized on a test area of the reagent carrier and analytes which are present in a sample liquid wetting the test area are detected. These reagent carriers which are also referred to as chips in the following must be treated and handled in a protected manner until their intended use so that undesired contamination is avoided and the reactants retain their specific binding capability for the sample analytes.

The base housing of the reagent carriers can be formed from a variety of solid materials and especially also from plastic.

Such plastic chips can for example, after their manufacture in an injection molding process, be coated with "dry chemistry" for example using a microspot method in order to immobilize the reactant molecules on the test area of the chip. Such a coating usually takes place automatically in a coating plant. After the coating and drying the chips are prepared ready for use. They then have to be placed in a package which offers them protection against environmental influences.

Several weeks may indeed pass before the individual chips are used for medical or chemical investigations. Thus, high demands must be made on the packaging with regard to screening chips against environmental influences such as varying air humidity, varying temperature, dust etc.

Furthermore, it should be possible to automatically handle the packaging when it is loaded with the newly manufactured chips in automatic filling machines as well as when the chips are used by customers in analyzers. The automated processes when the packaging is filled by the manufacturer and when the chips are used by customers, should be designed to be as simple and space-saving as possible.

SUMMARY OF THE INVENTION

It is against the above background that the inventors envisage that packaging should be suitable for accommodating and securing a plurality of chips in such a manner that, after opening the packaging for use, some but not all chips that are not intended to be used immediately can continue to remain protected in the packaging until they need to be used.

These requirements are fulfilled by a packaging cassette for reagent carriers according to the invention which is characterized by a base housing comprising connected adjacent compartments for reagent carriers and in particular compartments that are arranged side by side or/and above one another, wherein the compartments are separated from one another by partitions and are opened individually, each compartment having its own sealing cover which enables the compartment to be re-sealed.

The cassette geometry allows a space-saving and low-priced implementation of a packaging cassette where the arrangement of the compartments in rows facilitates an automated handling of the packaging cassette. Since the individual compartments can be opened separately from one another, in an analytical process it is possible in each case to use as many chips from the cassette as are required for the analytical process without exposing the other chips in the cassette to environmental influences which would thus also have to be consumed. Each compartment of the packaging cassette has its own sealing cover which enables the compartment to be re-sealed. The ability to re-seal the compartments can for example be utilized when the reagent carriers are being prepared by the manufacturer in that for example in a case reagent carriers that have not yet been prepared with reactants are delivered in the packaging cassette and then coated with the relevant reagents either outside the packaging cassette or optionally within the packaging cassette and after coating and drying, finally accommodated again in a protected state in the packaging cassette. The possibility of re-sealing the individual compartments of the packaging cassette should anyway be provided if the packaging cassette should not only be used as a disposable product but as a packaging cassette which can again be filled after use. However, the packaging cassette according to the invention is preferably a disposable packaging cassette which after its reagent carriers have been used, is also treated as used and transferred to the recycling waste. In this connection it may be the case that the used reagent carriers should also remain in the packaging cassette. The ability to re-seal the compartments is also important for this case.

According to one embodiment of the invention, the sealing covers and the base housing of the packaging cassette have closure elements that are assigned and complementary to one another and sealingly engage one another in a clamping or snap-fit manner when the compartments are closed by the sealing covers. Such snap closure elements can be simply molded on or can be formed together with the base housing and the sealing covers in a common manufacturing process. The closure elements can additionally adopt the sealing function so that the compartments in a closed state are very-well sealed against the effects of external humidity and dust.

In one manner the sealing covers are hinged lids which are hinge-mounted on the base housing. Hinged lids have the advantage that they can be manually as well as automatically handled with simple means and are undetachably located on the base housing. In this connection a special variant of the packaging cassette is recommended in which the base housing and the hinged lid are manufactured interconnected as one piece and especially as a one piece injection-molded product. The pivotability of the hinged lids for the opening and closing movements can be ensured by "film hinges" i.e. by thin-walled transitions between the sealing covers and the base housing. The packaging cassette is preferably made of a plastic. In this connection it may be expedient according to one embodiment of the invention to manufacture the packaging cassette from the same material as the reagent carriers that have not yet been prepared with reagents. Thus, the packaging cassette and reagent carrier bodies can be derived from one and the same original production.

As already mentioned the injection-molding technique is one manufacturing technique for the packaging cassette and optionally the reagent carriers although other production processes such as the blow-molding technique also come into consideration. This does not exclude the possibility that the packaging cassette and the reagent carrier body are produced from different materials and originate from different productions.

Each sealing cover is preferably provided with an operating tab where the essentially identically designed operating tabs of the sealing covers assigned to one row of compartments are next to one another or above one another in sequence and project beyond one edge of the base housing towards the outside in the closed state. The actuating tabs facilitate the engagement of the sealing covers when the compartments are manually or optionally mechanically opened and closed. Furthermore, the operating tabs arranged as described above facilitate the simultaneous mechanical opening and closing of several and optionally all compartments if this is desired.

With regard to simplifying the production and using material economically, it is proposed that the base housing essentially consists of a base plate in which all the compartments or optionally groups of compartments are impressed as depressions aligned relative to one another in a row which are to be closed by the molded-on hinged lids. The reference to the depressions aligned relative to one another in a row optionally in groups is intended to show that the packaging cassette can have several rows of compartments. However, one embodiment of the invention provides a single row arrangement of essentially identically designed compartments.

The compartments are preferably dimensioned and optimized with regard to space requirements such that they can each essentially hold only one single reagent carrier and optionally a small desiccant store. With regard to space optimization which should comprise a reduction of the air space surrounding the reagent carrier in its closed compartment, the sealing covers may have inwardly projecting bulges which fill out the space in the compartment in the closed state that is not occupied by the reagent carrier.

Each compartment is preferably assigned a desiccant reservoir which can hold a quantity of a desiccant e.g. hygroscopic material. The desiccant reservoir of a compartment can for example be formed in a depression of the sealing cover where at least one communication opening to the interior of the compartment is provided in the depression. The depression and desiccant which may be located therein is closed to the outside by a sealing foil which in one variant of the invention can be removed as needed. A desiccant reservoir can be alternatively or additionally provided in the bottom area of the base housing whereby also in this case trough-shaped bulges with communication holes can form the desiccant reservoirs. The desiccant reservoirs in the bottom area of the base housing are also sealed towards the outside by sealing foils. The hollow spaces or depressions described above as desiccant reservoirs can alternatively or additionally also be used as reservoirs for liquid reagents or dry reagents which are assigned to the reagent carriers.

The packaging cassette can be directly printed on or written on for example by inkjet or suchlike. Adhesive foils or sealing foils are also suitable as information carriers on the packaging cassette.

Embodiment examples of the invention are elucidated further in the following with reference to the figures.

BRIEF DESCRIPTION OF THE DRAWINGS

FIG. 1 shows a first embodiment example in a packaging cassette according to the invention in a perspective view from above with opened and closed compartments for reagent carriers.

FIG. 2 shows the packaging cassette from FIG. 1 in a perspective view from below.

FIG. 3 shows a second embodiment example of a packaging cassette according to the invention in a perspective view from above.

FIG. 4a-4c show a third embodiment example of a packaging cassette according to the invention in perspective views in which FIG. 4a shows the packaging cassette in a partially closed state with a view of the front side, FIG. 4b shows the packaging cassette in a completely opened state in a similar perspective to FIG. 4a, and FIG. 4c shows the packaging cassette in a view showing the rear side.

DETAILED DESCRIPTION

FIG. 1 shows a packaging cassette 1 which has a base housing 3 with 20 compartments 5 arranged side by side for reagent carriers 7 where the compartments 5 are separated from one another by partitions 9. Each compartment is allocated its own sealing cover 11 which allows an optional closing or opening of the respective compartment. In FIG. 1 the lower five compartments 5 in the drawing sheet are shown in an open state, whereas the remaining compartments 5 are shown in a closed state.

The lowest two opened compartments 5 are empty in this example i.e. shown without a reagent carrier in order to better illustrate the trough shape of the compartments 5 in the base housing 3. Reagent carriers 7 are drawn in the remaining opened compartments 5 in order to indicate their secured packaging position. The loading of the compartments 5 and the removal of the reagent carriers 7 from the compartments 5 usually takes place from above in the embodiment example shown.

The base housing 3 that is shown and the sealing covers 11 that are hinged thereon by film hinges 12 are produced as a connected unit in an injection-molding process.

The packaging cassette from FIG. 1 and FIG. 2 is intended to be used in an essentially horizontal orientation so that the openings of the compartments 5 are at the top and on a common horizontal plane.

The sealing covers 11 have a circular circumferential sealing lip 13 that matches the edge contour of the compartment depressions 5 which, when the compartment is closed, makes a clamping fit with or snaps into an upper step-shaped widening 15 of the compartment depression 5. In this manner the respective compartment 5 is reliably closed and sealed towards the outside. When the compartments 5 are in a closed state, a tab section 14 provided at the free end of the sealing covers projects outwards over the edge 17 of the base housing 3 that is distant to the hinges 12 of the sealing covers. The tabs 14 facilitate the manual or mechanical gripping of the sealing covers 11 in order to open the compartments 5 individually or in groups or altogether.

The reagent carrier chips 7 shown in FIG. 1 each have a trough-like depression 21 the bottom of which forms a test area zone in which a coating with immobilized reagents is provided for later analyses. The reagent carrier chips 7 shown are only intended to represent examples. The packaging cassette 1 could also be used to hold other types of chip.

The longitudinal sides 17, 18 of the base housing 3 have a continuous guide groove 23, 25 in the longitudinal direction which allows the packaging cassette to be moved in a guided manner on guide rails of automated loaders or automated analyzers. The view of the underside of the packaging cassette 1 according to FIG. 2 shows that depressions 27 are also impressed into the bottom of the base housing 3 such that under each compartment there is a depression 27 on the underside. These depressions 27 are used to hold a desiccant in order to keep the compartments 5 dry. A connecting hole 29 is provided between these desiccant reservoirs 27 and their allocated compartments 5 in order that any moisture in a particular compartment 5 can reach the desiccant reservoir 27. The embodiment example of FIG. 1 could be modified such that the partitions between the desiccant reservoirs 27 are omitted in order to form larger desiccant reservoirs which are then allocated to several compartments 5.

The depressions 27 have to be sealed towards the outside with a sealing foil 31 which is shown separately in FIG. 2 and can for example be a vapor-impermeable aluminum-laminated sealing foil. Test-specific information, labels, marks etc. can for example be printed on the sealing foil.

The embodiment example in FIG. 3 differs from the embodiment example described above in that reservoir depressions 27 for desiccants are provided in the hinged lid closures 11. The dimensions of the reservoir depressions 27 are such that they can engage in the trough area 21 of the reagent carrier chips 7 when the relevant sealing cover 11 is brought into a closed position. This not only has the advantage that the desiccant in the reservoir 27 can be moved near to the areas of the reagent carrier chips 7 that have to be kept dry and that furthermore the air volume in the closed compartments 5 is kept very small. Communication holes 29 are provided between the desiccant reservoirs 27 and the compartments 5. The desiccant reservoirs 27 are sealed towards the outside with strips of sealing foil 31a, three of which are shown in a lifted state in order to more clearly show the reservoir depressions 27. Information can be printed on the strips of sealing foil 31a such as test-specific information, marks etc.

The packaging cassette from FIG. 3 is otherwise designed essentially as the packaging cassette from FIG. 1. Hence, the reference numerals assigned to functionally identical elements in FIG. 1 have been used to label corresponding elements in FIG. 3. Therefore, the description of FIGS. 1 and 2 can be basically used to understand FIG. 3.

One of the design variants of the packaging cassette that is not shown in the figures has no separate depressions as desiccant reservoirs in the sealing covers and bottoms of the compartments. In these design variants space can be reserved within the compartment for desiccant if desiccant is to be used at all.

Furthermore, reference is also made to a variant which largely corresponds to the packaging cassette of FIG. 3 where, however, the depressions 27 in FIG. 3 have no holes 29 connecting them to the compartments 5 and therefore do not serve as desiccant reservoirs. They are nevertheless expedient because they reduce the air space volume of the compartments 5.

This latter variant can for example be set up to hold liquid reagents or dry reagents in the depressions 27 which are allocated to the reagent carriers. In the case of such a modification of the embodiment shown in FIG. 3, preferably pre-prepared and initially closed communication openings should be provided in the bottoms of the depressions 27. These can for example be communication openings that have to be pierced and thus opened and then allow the passage of the respective liquid reagents or optionally dry reagents to the allocated reagent carriers and thus to their test areas.

A further embodiment example of a packaging cassette according to the invention is shown in FIGS. 4a-4c in perspective diagrams. In FIGS. 4a-4c elements whose function corresponds to that of elements in FIGS. 1-3 are labeled with the respective reference numbers increased by 100.

The packaging cassette 101 is designed to be used in an upright arrangement so that the row of adjacent compartments 105 is aligned essentially vertically. In contrast to the embodiment examples of FIGS. 1-3, the reagent carriers 107 do not lie in a horizontal plane side by side in their storage position in the packaging cassette 101 but rather in parallel planes above one another. The compartments 105 in the base housing 103 can be used as drawers so that the reagent carriers 107 can be inserted into and pushed out of the compartments 105 in a horizontal direction. In FIG. 4c 32 openings can be seen in the rear side of the packaging cassette 101 through which an ejector bolt can push a respective reagent carrier 107 out of the front opening 34 and thus deliver it to a transfer unit of an analytical system. However, the compartments 105 are designed such that reagent carriers can be inserted and also removed through the front openings 34 by means of gripping devices or for example suction lifters.

The reagent carriers 107 from FIG. 4b can correspond to the reagent carriers from FIG. 1.

The compartments 5 separated from one another by the partitions 109 can be opened or closed individually which is why the sealing covers 111 are provided. These sealing covers 111 are in principle constructed exactly as the sealing covers 111 in FIG. 1. The sealing covers 111 are connected to the base housing 103 by film hinges 112 so that they can be folded around their vertical hinge axes in order to close or to open the compartments 105. FIG. 4b also shows that the sealing covers 111 have a sealing ring 113 that matches the edge contour of the openings 34 and makes a clamping fit on the respective opening 34 or snaps into the opening 34 when the respective compartment 105 is closed. When the compartments 105 are in a closed state, a tab section 114 provided at the free end of the sealing covers projects outwards over the edge 117 of the base housing 103 that is distant to the hinges 112 of the sealing covers 111. The tabs 114 facilitate the manual or mechanical gripping of the sealing covers 111 in order to open the compartments 105 individually or in groups or altogether. 45 in FIG. 4a designates a snap connection element in the form of a snap hook sticking out from the cover 111 which makes a snap-fit engagement with a bar 46 provided as a complementary snap connection element on the front side of the housing 103 when the respective cover 111 is closed. The snap connection 45, 46 secures the sealing of the compartments 5 in the closed state.

As shown in FIG. 4b each compartment 105 is allocated a desiccant reservoir 127 which is located horizontally at the side thereof and communicates with the relevant compartment 105 by means of a connecting hole 129. A first sealing foil 131 seals the desiccant reservoirs 127 towards the outside. In FIG. 4a this sealing foil 131 is shown in a glued state on the side 36 of the base housing 103 which has the openings of the desiccant reservoirs. The sealing foil 131 is not shown in FIGS. 4b and 4c for the sake of clarity.

It should also be noted that the ejector openings 32 are also closed by a sealing foil which is shown in FIG. 4c next to the base housing 103 in an as yet unglued state and is labeled with the reference numeral 38.

An upper handgrip 40 facilitates the manual or optionally the mechanical handling of the packaging cassette 101. A centering star 42 is also provided at the lower end which serves to accurately position the base housing 103 in the analytical system or in an automatic loader.

The base housing 103 is preferably constructed in one piece together with the sealing cover flaps 111 and for example produced in an injection-molding process. It is therefore preferably made of a plastic. In a variant of the embodiment example of FIG. 4a-4c that is not shown, two or more rows of compartments arranged above one another can be provided such that in a top-view the compartments form a two-dimensional matrix. A modification of the embodiment example of FIG. 4a-4b would also be conceivable according to which two compartments in series are provided in each plane, the covers of which are arranged on opposite sides of the base housing.

The dimensions of the embodiment example according to FIG. 4a-4c are such that each compartment can hold no more than one reagent carrier 107. In one variant of the embodiment example two or more reagent carriers 107 may fit into one compartment 105.

The packaging cassette according to the invention can be used in automated devices and is thus suitable for accompanying the complete lifetime of the reagent carriers from their production by injection-molding through the coating until they are processed on a customer's instrument system and are disposed of there.

This may occur in the following manner:
the still uncoated reagent carrier bodies are manually or automatically inserted into the packaging cassette and the compartments are closed;
the reagent carriers are transported in the packaging cassette to the coating plant;
the cassette covers are fully automatically opened and the reagent carriers are transferred from the cassette onto a coating carriage;
after the coating, the reagent carriers are fully automatically transferred back from the coating carriage into the packaging cassette and the cassette compartments are closed by folding down the sealing covers;
alternatively the reagent carriers can be coated in the packaging cassette i.e. remain in the packaging cassette during the coating process;
the packaging cassette is provided with desiccant and labeled;
the cassette is loaded into an outer packaging;
the cassette with the prepared reagent carriers is transported to the customer;
the customer inserts the cassette with the reagent carriers into his analytical system;
the individual sealing covers are opened fully automatically in the analytical system and the respective reagent carriers are removed fully automatically from the packaging cassette for the purposes of channeling them into the process;
after the processing and thus after the analyses have been carried out on all reagent carriers, the analyzer discards the reagent carriers and the cassette into a container for recycling waste.

In the example of FIGS. 1-4 the sealing covers were provided with a sealing lip to seal the compartments and ensure a closed state. Alternatively or in addition a "bead" connection can for example also be provided for sealing.

In the embodiment examples described above each individual chip was provided with its own compartment.

Another embodiment provides that two or more chips are accommodated in each compartment.

Furthermore, predetermined breaking points can be provided between compartments which enable the cassette to be divided as required.

Another embodiment of a packaging cassette according to the invention that is not shown has a circular or ring-shaped configuration which could for example be obtained by modifying the essentially linear cassette from FIG. 1 or FIG. 3 into a variant bent into a curve or circle. This can be a flat carousel variant with sealing covers located on top or a barrel variant with sealing covers located laterally on the circumference of the barrel.

It should be noted that the packaging cassette according to the invention can be designed to hold reagent carriers or similar small containers which can have a structure that deviates considerably from the reagent carriers 7 shown in the figures such as for example test strips, test tubes or other small containers for test chemicals or treating chemicals.

What is claimed is:

1. Combination of a packaging cassette and reagent carriers contained therein, said reagent carriers comprising a test area with reactants immobilized thereon, and said packaging cassette comprising a one-piece base housing, the base housing having longitudinal sides, each of the longitudinal sides having a continuous guide groove extending in a longitudinal direction substantially the entire length of the base, the guide grooves are directly opposing each other and have the same structural shape, and the base is moveable via guide rails via automated loaders or automated analyzers, the base housing comprising connected adjacent side by side compartments each of which is configured to completely accommodate therein, sealingly against environmental influences, at least one reagent carrier, the compartments are separated from one another by partitions and are configured to be opened individually, each of the compartments having a respective sealing cover pivotably connected to said base housing by an individually associated hinge and configured to be separately and repeatedly resealable; said packaging cassette further comprising at least one separate desiccant reservoir adjacent said respective compartments and in communication via respective connecting holes with said compartments, said desiccant reservoir being provided in a depression impressed into a bottom of the base of the housing under said respective compartments; and wherein the desiccant reservoir is entirely formed by the impression.

2. Combination according to claim 1, wherein said packaging cassette further comprises said desiccant reservoir containing a desiccant.

3. Combination according to claim 2, wherein the separate desiccant reservoir is trough-shaped and sealed by a sealing foil.

4. Combination according to claim 3, wherein the sealing covers extend into the compartments when the sealing covers are sealing the compartments.

5. Combination according to claim 1, wherein the separate desiccant reservoir is trough-shaped and sealed by a sealing foil.

6. Combination according to claim 1, wherein the respective sealing cover of each of the compartments and the base housing have closure elements that are assigned and complementary to one another and sealingly engage one another when each of the compartments are closed by their respective sealing cover.

7. Combination according to claim 1, wherein each sealing cover and the base housing are manufactured interconnected as one piece.

8. Combination according to claim 1, wherein each sealing cover and the base housing are manufactured interconnected as a one piece injection-molded product.

9. Combination according to claim 1, wherein each sealing cover is provided with an operating tab, and wherein operating tabs of the sealing covers assigned to one row of compartments are next to one another or above one another in sequence and project beyond one edge of the base housing towards the outside in the closed state.

10. Combination according to claim 1, further comprising a base plate in which all the compartments are in the form of depressions that are aligned relative to one another in a row.

11. Combination according to claim 1, wherein each of the compartments is dimensioned to hold only one single reagent.

12. Combination according to claim 1, wherein the packaging cassette is a plastic.

13. Combination according to claim 1, wherein each of the reagent carriers comprises a trough-like depression the bottom of which forms the test area coated with the reactants.

14. Combination of a packaging cassette and reagent carriers contained therein, said reagent carriers comprising a test area with reactants immobilized thereon, and said packaging cassette comprising a one-piece base housing, the base housing having longitudinal sides, each of the longitudinal sides having a continuous guide groove extending in a longitudinal direction substantially the entire length of the base, the guide grooves are directly opposing each other and have the same structural shape, and the base is moveable via guide rails via automated loaders or automated analyzers, the base housing comprising connected adjacent side by side compartments each of which is configured to completely accommodate therein, sealingly against environmental influences, at least one reagent carrier, the compartments are separated from one another by partitions and are configured to be opened individually, each of the compartments having a respective sealing cover pivotably connected to said base housing by an individually associated hinge and configured to be separately and repeatedly resealable, said packaging cassette further comprising at least one reagent reservoir adjacent said respective compartments and being separated by a separation wall including a pre-prepared initially closed communication opening, said reagent reservoir containing a reagent; said packaging cassette further comprising at least one separate desiccant reservoir adjacent said respective compartments and in communication via respective connecting holes with said compartments, said desiccant reservoir being provided in a depression impressed into a bottom of the base of the housing under said respective compartments; and wherein the desiccant reservoir is entirely formed by the impression.

15. Combination according to claim 14, wherein the sealing cover extends into one of the side by side compartments when the sealing cover is sealing one of the compartments.

16. Combination according to claim 15, wherein the separate desiccant reservoir is trough-shaped and sealed by a sealing foil.

17. Combination according to claim 14, wherein each sealing cover and the base housing are manufactured interconnected as a one piece injection-molded product.

18. Combination according to claim 14, further comprising a base plate in which all the compartments are in the form of depressions that are aligned relative to one another in a row.

19. Combination according to claim 14, wherein each of the compartments is dimensioned to hold only one single reagent.

20. Combination according to claim 1, wherein each of the compartments is dimensioned to hold only one single reagent carrier and a small store of desiccant.

21. Combination according to claim 14, wherein each of the compartments is dimensioned to hold only one single reagent carrier and a small store of desiccant.

* * * * *

UNITED STATES PATENT AND TRADEMARK OFFICE
CERTIFICATE OF CORRECTION

PATENT NO. : 9,457,349 B2
APPLICATION NO. : 12/168553
DATED : October 4, 2016
INVENTOR(S) : Stephan Sattler et al.

It is certified that error appears in the above-identified patent and that said Letters Patent is hereby corrected as shown below:

On the Title Page

(75) Inventors: "Stephan Sattler, Stamberg (DE); Reinhold Krämer, Peissenberg (DE)"
Should read:
(75) Inventors: --Stephan Sattler, Starnberg (DE); Reinhold Krämer, Peissenberg (DE)--.

Signed and Sealed this
Sixth Day of February, 2018

Joseph Matal
*Performing the Functions and Duties of the
Under Secretary of Commerce for Intellectual Property and
Director of the United States Patent and Trademark Office*